United States Patent [19]

Danek

[11] 4,303,076
[45] Dec. 1, 1981

[54] PROBE FOR TRANSCUTANEOUS SAMPLING

[75] Inventor: Josef Danek, Doylestown, Pa.

[73] Assignee: Air Shields, Inc., Hatboro, Pa.

[21] Appl. No.: 108,800

[22] Filed: Dec. 31, 1979

[51] Int. Cl.³ .............................................. A61B 5/00
[52] U.S. Cl. ................................ 128/635; 204/195 B; 204/195 P
[58] Field of Search ............................ 128/635, 632; 204/195 B, 195 P

[56] References Cited

U.S. PATENT DOCUMENTS

| | | | |
|---|---|---|---|
| 3,659,586 | 5/1972 | Johns et al. | 128/635 |
| 3,795,239 | 3/1974 | Eberhard et al. | 128/635 |
| 4,005,700 | 2/1977 | Parker | 128/632 |
| 4,175,028 | 11/1979 | Payton | 204/195 P |
| 4,185,620 | 1/1980 | Hagihara | 128/635 |
| 4,197,853 | 4/1980 | Parker | 128/635 |
| 4,207,160 | 6/1980 | Frankenberger et al. | 128/635 |

FOREIGN PATENT DOCUMENTS 2920038  11/1979  Fed. Rep. of Germany ...... 128/635

OTHER PUBLICATIONS

Scacci et al., "Oxygen Tension Monitoring", Med. Inst., vol. 10, No. 4, pp. 192-194, Jul.-Aug. 1976.
Eberhard et al., "An Intro. . . . $O_2$ Monitoring in the Neoncte", Hoffman-LeRoche & Co., pp. 1-34, 1976.

Primary Examiner—Lee S. Cohen
Attorney, Agent, or Firm—Weiser, Stapler & Spivak

[57] ABSTRACT

A probe for transcutaneous blood gas analysis composed of a housing (10) and a cap (18) which are assembled together by a snap-fit. The housing (10) holds an electrode unit (38, 40, 42) and the cap (18) carries a membrane (30) which spans an opening (20) in the cap (18) through which the electrode unit (38, 40, 42) projects. The membrane (30) contains an electrolyte between the electrode unit (38, 40, 42) and the membrane (30).

27 Claims, 2 Drawing Figures

PROBE FOR TRANSCUTANEOUS SAMPLING

DESCRIPTION

1. Technical Field

The present invention relates, in general, to transcutaneous monitoring of blood gases and, in particular, to a probe which is placed against the skin of a patient to sense blood gases diffusing through the skin. Although the invention will be described in connection with the measurement of the partial pressure of oxygen ($pO_2$), it will be apparent that the underlying concepts of the invention may be applied to measure other parameters of the blood, such as the partial pressure of carbon dioxide ($pCO_2$).

2. Background Art

The importance of blood gas analysis is well known. Various body disorders can be identified through such an analysis. For example, the status of the respiratory function may be determined by examining blood gases. Also, metabolic disorders, such as kidney failure, can be monitored by blood gas measurements. Careful examination of blood gases, particularly the partial pressure of oxygen, is important for infants undergoing oxygen therapy.

A common technique for conducting blood gas analysis involves drawing a blood sample from the patient. One way to do this is to use a catheter in the umbilical artery. An alternative is to draw capillary blood from a heel prick after the capillaries and arterioles have been dilated. Still another alternative is to draw the blood from another artery, such as the radial artery. Regardless of the manner in which the blood sample is obtained, once drawn, the blood must be kept isolated from the atmosphere and stored on ice.

There are a number of limitations and shortcomings to drawing blood samples for blood gas analysis. First, the monitoring of the blood gases is not continuous. Experiments have shown that the partial pressure of oxygen can change quickly and significantly, so that even blood samples drawn two or three times an hour cannot always provide the trend information needed to determine the effects of therapy. Another problem with drawing blood samples is that the procedure is invasive and, therefore, may cause significant complications such as thrombosis or emboli. Yet another concern is that repeated blood samplings may result in anemia and require transfusions. Finally, the overall cost of drawing and preserving the blood sample and conducting the blood gas analysis is higher than desired.

Transcutaneous blood gas measurement is a very attractive alternative to drawing blood samples for blood gas analysis. This technique is non-invasive and provides continuous blood gas monitoring. It utilizes a probe which is placed against the skin of a patient and upon sensing blood gas diffusing through the skin develops, by electrochemical means, an electrical signal representative of the partial pressure of the gas being sensed. A great deal of work has been performed over the last ten or so years in perfecting transcutaneous blood gas analysis. Much of this work has been concentrated in the area of probe design.

Typically, a probe in a transcutaneous blood gas analyzing system includes a pair of electrodes and an electrolyte for developing the signal representative of the gas diffusing through the skin, a membrane permeable to the gas diffusing through the skin for containing the electrolyte, heating means for heating the body tissue to increase blood circulation in the vicinity of the body where the probe is placed, and a heat sensor for developing an indication of the temperature of the body tissue in the vicinity of the probe. With time, the electrolyte and the membrane need to be replaced. Besides deterioration of the electrolyte and membrane, a portion of the electrolyte evaporates. Instead of replacing the entire probe which is quite expensive, the probe is designed to permit removal of the old electrolyte and membrane and introduction of fresh electrolyte and a new membrane.

Most of the approaches suggested in the past for changing the electrolyte and membranes of such probes have been found to be inadequate. This results from probe designs which do not lend themselves to easy electrolyte and membrane replacement and from poor concepts underlying the replacement feature design. For example, certain probes having a flat contact surface require the use of an electrolyte gel rather than an electrolyte liquid. Use of a gel requires a special tool to spread the gel which is a difficult and time-consuming operation for the user. Improper spreading of the gel will result in improper sensing of blood gas by the probe.

Some probes have been provided with caps which screw onto the main body to hold the electrolyte and membrane in place. Rotary action on the membrane tends to wrinkle the membrane which also will result in improper operation of the probe.

Still another problem with some of the probes which are available at the present time is that the handling and positioning of the membrane during replacement is awkward and difficult often leading to improper setting of the membrane within the probe. This again will lead to improper probe operation.

DISCLOSURE OF THE INVENTION

Accordingly, it is an object of the present invention to provide a new and improved probe for transcutaneous blood gas analysis.

It is another object of the present invention to provide a probe for transcutaneous blood gas analysis which is arranged for easy replacement of the probe electrolyte and probe membrane.

It is a further object of the present invention to provide a probe for transcutaneous blood gas analysis which is relatively simple in construction.

It is yet another object of the present invention to provide a probe for transcutaneous blood gas analysis which may be fabricated at reasonable cost.

These and other objects are achieved by a probe constructed in accordance with the present invention. Such a probe includes a housing and a cap having an axis common to the axis of the housing. The cap has an opening in its base and locking means which engage the housing upon movement of the cap along its axis for securing the cap to the housing. The probe also includes a membrane secured to the cap and spanning the opening in the base of the cap. The probe further includes detector means responsive to blood gas diffusing through the skin of a body against which the probe is positioned for developing an electrical signal representative of the blood gas. The detector means are composed of an electrode unit held within the housing and forming a domed surface which projects from the housing through the opening in the base of the cap and an electrolyte between the domed surface and the membrane. The probe further includes sealing means positioned between the housing and the membrane for preventing the electrolyte from escaping and means emanating from the housing for conducting the electrical signal developed by the detector means to a remote location.

The arrangement of the probe is such that when the electrolyte and membrane need to be replaced, the cap and housing are separated and the domed surface formed by the electrode unit is cleaned. New electrolyte is deposited either on the domed surface or on a new membrane and the new membrane carried by a new cap is brought into position by engagement of the locking means on the cap with the housing as the cap is moved axially into contact with the housing.

BRIEF DESCRIPTION OF DRAWING

Referring to the drawing.

BEST MODE FOR CARRYING OUT THE INVENTION

Figure 1:
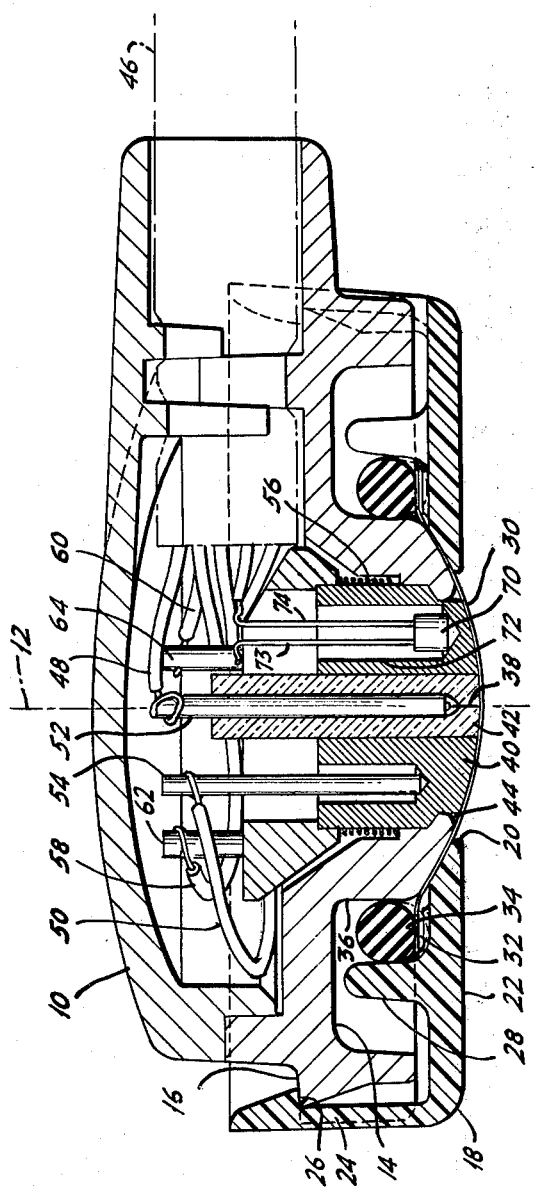
FIG. 1 is a vertical section of a probe constructed in accordance with the present invention.

Referring to the drawing, a probe constructed in accordance with the present invention includes a housing 10 preferably fabricated from a suitable plastic material which functions as an insulator and also permits manufacture of the housing at relatively low cost. Housing 10 is generally disc-shaped and has an axis of rotation 12. The bottom surface of housing 10 is formed with a groove 14 and the peripheral edge of the housing is formed with a shoulder 16.

Figure 2:
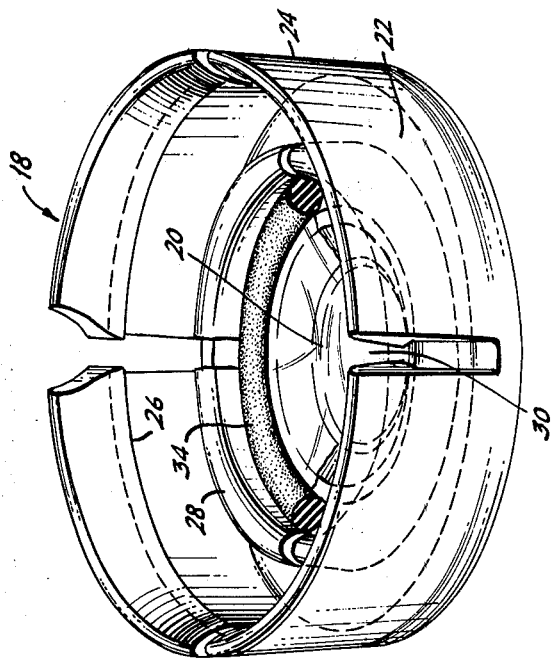
FIG. 2 is a perspective view of the cap portion of the FIG. 1 probe.

A probe constructed in accordance with the present invention also includes a cap 18, shown in FIGS. 1 and 2 as being generally cup-shaped and having an opening 20 in its base 22. Cap 18 also is preferably fabricated from a plastic material. The axis of rotation of cap 18 is common to axis 12 of housing 10. Base 22 of cap 18 is perpendicular to axis 12. The side wall 24 of cap 18 is generally parallel to axis 12 and is formed with a lip 26 arranged to bear against shoulder 16 of housing 10. Lip 26 serves as a locking means for securing cap 18 to housing 10. Side wall 24 of cap 18 is slotted at a plurality of locations to enhance its flexibility. As cap 18 is moved along axis 12 into engagement with housing 10, side wall 24 flexes radially outward until lip 26 passes over shoulder 16 and snaps back in a radially inward direction.

Cap 18 is formed with a circular ridge 28 surrounding opening 20. Ridge 28 is shaped, dimensioned and positioned so that it fits within groove 14 of housing 10 when the housing and the cap are assembled together.

The probe of the invention further includes a membrane 30 secured to cap 18 and spanning opening 20 in the cap. The attachment of membrane 30 to cap 18 is achieved by an adhesive layer 32 deposited on the inside surface of base 22 of the cap. Cap 18 also carries an O-ring 34 fitted over membrane 30 and inside ridge 28.

When cap 18 is secured to housing 10, O-ring 34 and ridge 28 fit within groove 14 in the housing. The arrangement is such that O-ring 34 is squeezed between ridge 28 of cap 18 and the inner wall 36 of groove 14. Adhesive layer 32 serves a second purpose. It seals the contents of the probe from the outside environment so that only blood gas penetrating membrane 30 enters the probe.

A probe constructed in accordance with the present invention also includes detector means responsive to blood gas diffusing through the skin of a body against which the probe is positioned for developing an electrical signal representative of the blood gas. The detector means include an electrode unit shown as comprising a cathode electrode 38 and an anode electrode 40 separated by an insulator 42. The electrode unit is held within housing 10 and is formed into a domed surface which projects from the housing through opening 20 in base 22 of cap 18. Thus, the domed surface formed by the electrode unit and membrane and the outside surface of base 22 of cap 18 form a face on the probe which is placed against a body. For the embodiment of the invention illustrated in FIG. 1, the domed surface of the electrode unit is spherical. However, other surfaces such as conical may be employed. In FIG. 1, cathode electrode 38 is in the form of a wire, insulator 42 is generally cylindrical and surrounds the cathode electrode, and anode electrode 40 is generally cylindrical and surrounds the insulator. Cathode electrode 38 may be platinum, while anode electrode 40 may be silver. Insulator 42 may be glass.

The detector means also include an electrolyte between membrane 30 and the spherical surface formed by the electrode unit. The electrolyte, in liquid form, may be an ethylene glycol solution which flows outwardly and spreads evenly between the spherical surface and the membrane as housing 10 and cap 18 are assembled together. Excess electrolyte flows into a reservoir 44 formed in housing 10 adjacent the outer edge of the spherical surface formed by the electrode unit. Any excess electrolyte which spreads beyond reservoir 44 is contained between membrane 30 and housing 10 by O-ring 34. As a result, electrolyte does not escape which would otherwise cause the detector means to dry out more quickly.

As oxygen permeates through membrane 30, it reacts chemically with the electrolyte. This reaction is sensed by the electrode combination and an electrical signal is developed having a magnitude representative of the amount of oxygen passing through the membrane. Because the nature of this chemical reaction is well known to those skilled in the art, additional explanation is not required.

One of the materials which may be used for membrane 30 is polypropylene. A characteristic of polypropylene is that it stretches in one direction easier than it does in a 90° direction. Thus, if a membrane made from polypropylene is disposed flat across opening 20 in cap 18, wrinkles will develop as the membrane is contacted and stretched by the spherical surface of the electrode unit when the housing and cap are assembled. Such wrinkles in the membrane will result in improper operation of the probe.

In order to prevent the development of such wrinkles, the membrane is preformed, preferably by stretching it into a generally spherical shape by a suitable tool. This tool is arranged with a radius of curvature greater than the radius of curvature of the spherical surface formed by the electrode unit. As a result, when housing 10 and cap 18 are assembled together, the prestretched membrane 30 is layed on the spherical surface in a progressive manner, starting in the center and moving radially outward. This causes the electrolyte to flow radially outward and spread evenly. The membrane undergoes slight additional stretching to finally conform to the spherical surface upon which it is being layed.

Cap 18 carrying membrane 30 and O-ring 34 may be assembled as follows. Adhesive layer 32 is deposited on the inside surface of base 22 inward of ridge 28. A piece of membrane material, approximately equal in size to the area defined inward of ridge 28, is placed over opening 20 in cap 18 and adhesive layer 32. As the membrane is prestretched into a generally spherical shape, its perimeter is held to prevent radially inward movement and wrinkling. After the membrane is stretched, O-ring 34 is snapped into place over the membrane, inward of ridge 28.

Also included in the FIG. 1 probe are means emanating from housing 10 for conducting the electrical signal developed by the detector means to a remote location. Such means may include a cable 46 composed of a pair of wires 48 and 50 secured to terminals 52 and 54, respectively, which, in turn, are in electrical contact with cathode electrode 38 and anode electrode 40, respectively. Wires 48 and 50 are connected to a recording system or display unit or the like which, in response to the electrical signal developed in the probe, provides a user with an indication of the blood gas diffusing through the skin of a body against which the probe is placed.

In order to increase the blood circulation in the vicinity of the body at which the probe is positioned, the probe is provided with heating means for transmitting heat to the face of the probe. The heating means may include a wire winding 56 surrounding anode electrode 40 to which electrical power is supplied to heat the anode electrode. Thus, with anode electrode 40 heated, heat is transmitted to that portion of the spherical surface formed by the anode electrode which, in turn, causes that portion of the body contact by the probe face to be heated.

Winding 56 is connected to a source of electrical power through a pair of wires 58 and 60 connected, respectively, to a pair of terminal posts 62 and 64. Wires 58 and 60 may form part of cable 46 if the source of electrical power is at the same remote location as the unit which provides the blood gas indication.

The electrical power supplied to winding 56 is regulated by a thermistor 70 which senses the temperature at the face of the probe and develops an electrical signal representative of this temperature. In particular, thermistor 70 is positioned in a recess 72 in anode electrode 40 near the spherical surface. The electrical signal developed by thermistor 70 is conducted to the source of electrical power by means of a pair of wires 73 and 74 which also may be a part of cable 46.

In actual use, when the electrolyte and membrane of the probe need to be replaced, cap 18 is detached from housing 10 by pulling lip 26 of the cap outwardly away from engagement with shoulder 16 of the housing. A new cap having a fresh membrane is snapped into place on housing 10 after fresh electrolyte has been deposited either on the membrane or on the spherical surface formed by the electrode unit. The economics are such that the cap, membrane and O-ring combination may be disposable. However, if feasible used caps may be returned to the manufacturer to salvage the cap and O-ring components.

As previously stated, the present invention has been described in connection with the measurement of the partial pressure of oxygen ($pO_2$). It will be apparent that with suitable modifications (e.g. different electrode materials), the invention has broader application, such as in the measurement of carbon dioxide ($pCO_2$).

While in the foregoing there has been described a preferred embodiment of the invention, it should be understood to those skilled in the art that various modifications and changes can be made without departing from the true spirit and scope of the invention as recited in the claims.

I claim:

1. A probe comprising:
a housing;
an electrode unit held within said housing and forming a domed surface which projects from said housing;
a cup-like cap having an opening in the base thereof through which said domed surface projects and a lip engaging said housing by a snap fit to secure said cap to said housing;
a membrane secured to said cap and spanning said opening in said base of said cap;
an electrolyte between said domed surface and said membrane;
sealing means positioned between said housing and said membrane for preventing said electrolyte from escaping;
and means for electrically connecting said electrode unit to a remote location.

2. A probe according to claim 1 wherein said domed surface is spherical.

3. A probe according to claim 2 wherein said cap has a circular ridge surrounding said opening and said sealing means include an O-ring positioned over said membrane and within said circular ridge.

4. A probe according to claim 3 wherein said housing has a groove surrounding said spherical surface and said ridge of said cap and said O-ring are fitted within said groove to squeeze said O-ring between said ridge and a wall of said groove within said O-ring.

5. A probe according to claim 2 wherein said electrode unit includes a cathode electrode and an anode electrode separated by an insulator.

6. A probe according to claim 5 wherein said cathode electrode is a wire, said insulator is generally cylindrical and surrounds said cathode, and said anode is generally cylindrical and surrounds said insulator.

7. A probe according to claim 6 wherein said cap has a circular ridge surrounding said opening and said sealing means include an O-ring positioned over said membrane and within said circular ridge.

8. A probe according to claim 7 wherein said housing has a groove surrounding said spherical surface and said ridge of said cap and said O-ring are fitted within said groove to squeeze said O-ring between said ridge and a wall of said groove within said O-ring.

9. A probe according to claim 4 wherein said membrane extends under said O-ring to said ridge of said cap and is secured to said base of said cap by an adhesive layer.

10. A probe adapted to be positioned against a body to detect a blood gas diffusing through the skin of said body, said probe comprising:
a housing;
a cap having an axis common to the axis of said housing and an opening in the base thereof, said cap also having locking means engaging said housing upon movement of said cap along said axis for securing said cap to said housing;
a membrane secured to said cap and spanning said opening in said base of said cap;

detector means responsive to said blood gas diffusing through said skin for developing an electrical signal representative of said blood gas, said detector means including an electrode unit held within said housing and forming a domed surface which projects from said housing through said opening in said base of said cap and an electrolyte between said domed surface and said membrane;

sealing means positioned between said housing and said membrane for preventing said electrolyte from escaping;

and means emanating from said housing for conducting said electrical signal developed by said detector means to a remote location.

11. A probe according to claim 10 wherein said domed surface is spherical.

12. A probe according to claim 11 wherein said cap has a circular ridge surrounding said opening and said sealing means include an O-ring positioned over said membrane and within said circular ridge.

13. A probe according to claim 12 wherein said housing has a groove surrounding said spherical surface and said ridge of said cap and said O-ring are fitted within said groove to squeeze said O-ring between said ridge and a wall of said groove within said O-ring.

14. A probe according to claim 10 wherein said electrode unit includes a cathode electrode and an anode electrode separated by an insulator.

15. A probe according to claim 14 wherein said cathode electrode is a wire, said insulator is generally cylindrical and surrounds said cathode, and said anode is generally cylindrical and surrounds said insulator.

16. A probe according to claim 13 wherein said membrane extends under said O-ring to said ridge of said cap and is secured to said base of said cap by an adhesive layer.

17. A probe having a face adapted for contact with the skin of a body, said probe comprising:

a cap having an axis common to the axis of said housing and an opening in the base thereof, the outside surface of said base forming a portion of said face, said cap also having locking means engaging said housing upon movement of said cap along said axis for securing said cap to said housing;

an electrode unit held within said housing and forming a domed surface which projects from said housing through said opening in said base of said cap and forms a portion of said face;

a membrane secured to said cap and spanning said opening in said base of said cap;

an electrolyte between said domed surface and said membrane;

sealing means positioned between said housing and said membrane for preventing said electrolyte from escaping;

first means emanating from said housing for electrically connecting said electrode unit to a remote location;

heating means held within said housing for transmitting heat to said face;

second means emanating from said housing for connecting said heating means to a source of electrical power;

sensing means held within said housing for sensing the temperature at said face and for developing an electrical signal representative of said temperature;

and third means emanating from said housing for connecting said sensing means to a remote location to conduct said electrical signal representative of said temperature to said remote location.

18. A probe according to claim 17 wherein said domed surface is spherical.

19. A probe according to claim 18 wherein said heating means include a wire winding surrounding said electrode unit.

20. A probe according to claim 18 wherein said electrode unit includes a wire cathode, a generally cylindrical insulator surrounding said cathode, and a generally cylindrical anode surrounding said insulator.

21. A probe according to claim 20 wherein said heating means include a wire winding on said anode and heat is transmitted to said spherical surface.

22. A probe according to claim 21 wherein said cap has a circular ridge surrounding said opening and said sealing means include an O-ring positioned over said membrane and within said circular ridge.

23. A probe according to claim 22 wherein said housing has a groove surrounding said spherical surface and said ridge of said cap and said O-ring are fitted within said groove to squeeze said O-ring between said ridge and a wall of said groove within said O-ring.

24. A cap for a probe for transcutaneous blood gas analysis comprising:

a cup-like member having an opening in the base thereof; and a membrane secured to the insie surface of said base and having an unsupported, generally spherical shape projecting through said opening.

25. A cap according to claim 24 wherein said membrane is made from polypropylene.

26. A cap according to claim 24 wherein said cap has a circular ridge surrounding said opening and carries an O-ring positioned over said membrane and within said circular ridge.

27. A cap according to claim 26 wherein said membrane extends under said O-ring to said ridge of said cap and is secured to said base of said cap by an adhesive layer.

* * * * *

UNITED STATES PATENT AND TRADEMARK OFFICE
CERTIFICATE OF CORRECTION

PATENT NO. : 4,303,076
DATED : December 1, 1981
INVENTOR(S) : JOSEF DANEK

It is certified that error appears in the above—identified patent and that said Letters Patent is hereby corrected as shown below:

In column 5, line 34, cancel "contact" and substitute --contacted--;

In Claim 17, between line 42 and 43 insert the words a housing;

In Claim 24, line 44, cancel "insie" and substitute --inside--.

Signed and Sealed this

Sixteenth Day of February 1982

[SEAL]

Attest:

GERALD J. MOSSINGHOFF

*Attesting Officer*   *Commissioner of Patents and Trademarks*